Feb. 6, 1934. O. P. BLACKBURN Plant Pat. 86
PEACH
Filed Aug. 5, 1933
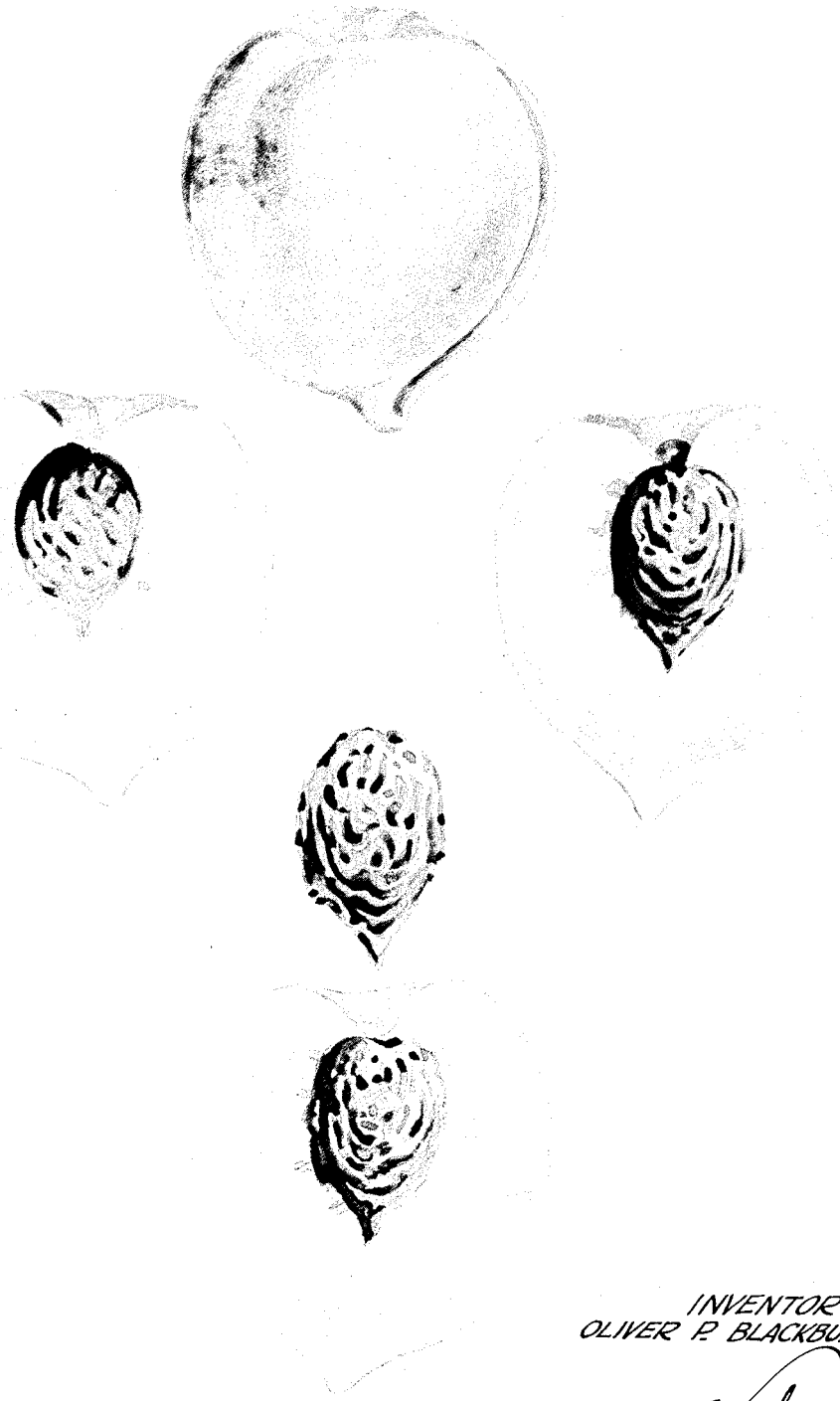
INVENTOR
OLIVER P. BLACKBURN
BY
ATTORNEY Patented Feb. 6, 1934

Plant Pat. 86

UNITED STATES PATENT OFFICE

86

PEACH

Oliver P. Blackburn, East Bakersfield, Calif.

Application August 5, 1933. Serial No. 683,806

1 Claim. (Cl. 47—62)

My invention relates to a new variety of peach tree.

The principal object of my invention is to produce a peach having excellent eating qualities, which is a full freestone peach, which is attractive to the eye, which has a relatively early ripening season, and which is relatively large in size.

The new variety of peach tree to which this application relates was originally grown from a self-pollinized seedling of a (red bird) Early Wheeler clingstone peach tree. This seedling was the result of a Stanwick nectarine tree and a (red bird) Early Wheeler clingstone peach tree growing in an orchard approximately twenty feet apart.

The planting of the original tree of my new variety of fruit above referred to was done by me during the year 1924. This original tree commenced bearing in 1927, and since that time has been asexually reproduced in the following manner. Scions, that is, buds, grafts, twigs, and branches of said original tree were budded or grafted onto suitable hardy rootstock and the trees thus produced have borne fruit of the exact type and kind produced by said original tree.

The new peach tree of my invention is of very high vitality and of strong growth. This tree is also hardy and resistant to parasite attacks and unfavorable weather conditions as compared to other peach trees.

New wood of my new peach tree of a season's growth has a clear green appearance with a pinkish tinge.

The foliage of my new peach tree has a very pronounced dark green color and the leaves have a decided curvature with slightly crinkled and notched edges.

The blossoms of my new peach tree are profuse, but the petals are relatively small, slender, and not fully expanded. These petals are of a very light pink color.

It is further desired to point out that there has been no tendency of the fruit thus produced to revert to either the nectarine or the (red bird) Early Wheeler clingstone peaches produced by the parents of the original tree of my new variety. Instead, the specimens of my new variety of peach produced on trees budded as aforesaid are quite uniform in quality, representative specimens of this fruit being shown in the accompanying drawing, in which:

The topmost figure is a perspective view of a whole representative peach of my new variety when thoroughly ripe.

The two figures immediately therebelow are elevational views of two halves of the peach shown in the uppermost figure after this peach has been separated on a vertical medial plane and showing the seed pocket in the left-hand half with the seed removed therefrom as it naturally and easily separates from said pocket with the division of the flesh of the fruit on said plane, the right-hand half having the seed still resting in the seed pocket thereof.

The next figure therebelow is a view of the seed by itself.

The bottom figure shows a half of another representative peach of my new variety which has less coloring in the meat thereof than the specimen shown in the uppermost figure.

The specimen of my new variety of peach in the upper three figures of the accompanying drawing is shown as when it reaches the market in fully ripe condition, in which condition a large portion of the peaches of this variety have the almost blood red coloring in the flesh of the fruit shown in this particular specimen. Before being fully ripe, however, the flesh of my peach is almost white and a certain portion of the peaches of this new variety particularly those on the inside of the tree, even when ripe, have a white or light cream flesh tinted with pink as indicated in the specimen shown in the lowermost figure of the drawing. These two specimens represent practically two extremes, and the interior coloring of my new variety of peach generally varies somewhere between these extremes. The specimen halves shown in the drawing have been torn apart so as to reveal the radial grain in the peach and the color in the flesh is shown as cloudy in places and as following the radial grain in others. It is to be understood, however, that when the peach is ripe but firm and free from bruises, and is then cut in half with a sharp knife, whatever color there is in the flesh appears on the cut surfaces in cloudy or diffused masses of irregular shapes which do not strongly reveal the radial grain of the flesh structure.

The peach of my new variety may be best distinguished from prior known varieties by a comparison with those which it most closely resembles. For instance, my new variety of peach is a full freestone peach and yet it resembles closely the (red bird) Early Wheeler clingstone peach in size and external coloring. It is thus considerably larger in size than the average freestone peach. My peach also has a relatively smaller seed than that of the (red bird) Early Wheeler clingstone peach, and this seed has a relatively long point.

My peach starts ripening just at the close of the harvest season of the (red bird) Early Wheeler clingstone peach so as to be the first full freestone peach on the market, and it is the only freestone peach at that season of ripening which resembles the (red bird) Early Wheeler clingstone peach in appearance. In southern California the first of the other freestone peaches which appear on the market are the St. John freestone peach and the Imperial freestone peach, and the latter two varieties do not ripen until my new variety of freestone peach is approximately half harvested, or a matter of a week or ten days after my new variety of peach has ripened.

The flesh of my new variety of peach is of a finer grain, is more tender, has a better flavor, and is juicier than that of the (red bird) Early Wheeler clingstone peach. The flesh of my new variety of peach is neither stringy nor mealy, but is firm and well adapted for shipping.

As to shape, the specimens illustrated in the drawing are representative, this indicating that the peach of my new variety is slightly more pointed at its lower end and has slightly more red color in the outer surface and in the grain of the flesh than the (red bird) Early Wheeler clingstone peach. The skin of my new variety of peach is also smoother and has less fuzz than that of the (red bird) Early Wheeler clingstone peach.

What I claim is:

A variety of freestone peach tree bearing fruit of the type herein shown and described, said fruit being characterized by a coloring resembling the (red bird) Early Wheeler clingstone peach, by a meat superior in eating qualities to that of the (red bird) Early Wheeler clingstone peach, by being a full freestone peach, and by a relatively early ripening season as compared with previously known freestone peaches.

OLIVER P. BLACKBURN.